US010315025B2

(12) United States Patent
Phillips et al.

(10) Patent No.: US 10,315,025 B2
(45) Date of Patent: Jun. 11, 2019

(54) AUTO-SHUTOFF COUPLING

(71) Applicant: Applied Medical Technology, Inc., Brecksville, OH (US)

(72) Inventors: Grant Wesley Phillips, Richfield, OH (US); Derek M. Williams, Cuyahoga Falls, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 314 days.

(21) Appl. No.: 14/554,505

(22) Filed: Nov. 26, 2014

(65) Prior Publication Data

US 2015/0157849 A1 Jun. 11, 2015

Related U.S. Application Data

(60) Provisional application No. 61/914,039, filed on Dec. 10, 2013.

(51) Int. Cl.
*A61M 39/26* (2006.01)
*A61M 39/10* (2006.01)
*F16L 37/30* (2006.01)

(52) U.S. Cl.
CPC .......... *A61M 39/26* (2013.01); *A61M 39/105* (2013.01); *A61M 2039/1033* (2013.01); *F16L 37/30* (2013.01)

(58) Field of Classification Search
CPC ................ A61M 39/26; A61M 39/105; A61M 2039/1033; F16L 37/30; F16L 37/32

(Continued)

(56) References Cited

U.S. PATENT DOCUMENTS 3,278,205 A * 10/1966 Barlow ............... F16L 37/1205
137/614
4,950,254 A 8/1990 Andersen et al.
(Continued)

FOREIGN PATENT DOCUMENTS

JP 2007-504850 A 3/2007
WO 2005/004974 A1 1/2005

OTHER PUBLICATIONS

International Search Report and Written Opinion of Corresponding International Application No. PCT/US2014/067595; dated Mar. 23, 2015.

(Continued)

*Primary Examiner* — Michael R Reid
*Assistant Examiner* — Patrick C Williams
(74) *Attorney, Agent, or Firm* — Pearne & Gordon, LLP

(57) ABSTRACT

The present disclosure relates to a breakaway coupling. A female adapter on a source side of the coupling uses a valve to prevent a flow of contents from the source when the coupling is not connected or is broken apart. A male adapter on a destination side uses a valve to prevent backflow from the destination when the female and male adapters are not coupled together. When coupled, the male adapter penetrates the valve of the female adapter, thereby allowing the flow from the source to the destination via the male and female adapters. Pressure from the flow opens the valve of the male adapter allowing the flow from the source to proceed to the destination. In the coupled state, the male and female adapters, and respective tubes, are able to rotate with respect to each other. The coupling may be used to deliver medical fluids to a patient.

10 Claims, 5 Drawing Sheets

(58) Field of Classification Search
USPC ..... 137/614.05, 614.02–614.06; 251/149.14; 604/533–539
See application file for complete search history.

(56) References Cited

U.S. PATENT DOCUMENTS

| | | | |
|---|---|---|---|
| 4,968,294 A | 11/1990 | Salama | |
| 5,280,876 A * | 1/1994 | Atkins | F16L 37/113 251/144 |
| 5,402,826 A * | 4/1995 | Molnar | B05B 5/1616 137/614.01 |
| 5,676,289 A | 10/1997 | Gross et al. | |
| 5,680,969 A | 10/1997 | Gross | |
| 5,688,254 A * | 11/1997 | Lopez | A61M 39/1011 604/529 |
| 5,797,523 A | 8/1998 | Gross | |
| 5,820,614 A * | 10/1998 | Erskine | A61M 5/16831 604/533 |
| 5,839,614 A | 11/1998 | Brown | |
| 5,839,626 A | 11/1998 | Gross et al. | |
| 5,934,512 A | 8/1999 | Lampe et al. | |
| 5,934,514 A | 8/1999 | Lampe et al. | |
| 5,938,086 A | 8/1999 | Gross | |
| 5,944,234 A | 8/1999 | Lampe et al. | |
| 5,954,237 A | 9/1999 | Lampe et al. | |
| 5,971,232 A | 10/1999 | Rohr et al. | |
| 6,006,960 A | 12/1999 | Gross | |
| 6,045,004 A | 4/2000 | Elliott | |
| 6,050,451 A | 4/2000 | Hess, III et al. | |
| 6,062,435 A | 5/2000 | Hess, III | |
| 6,065,642 A | 5/2000 | Brown | |
| 6,112,951 A | 9/2000 | Mueller | |
| 6,176,399 B1 | 1/2001 | Schantz et al. | |
| 6,354,564 B1 * | 3/2002 | Van Scyoc | F16L 37/32 137/614.04 |
| 7,077,296 B2 | 7/2006 | Brown et al. | |
| 7,537,024 B2 * | 5/2009 | Adams | C01B 3/065 137/614.03 |
| 7,892,216 B2 * | 2/2011 | Fangrow, Jr. | A61M 5/158 604/288 |
| 7,931,253 B1 * | 4/2011 | Paczonay | F16L 37/30 220/714 |
| 7,955,317 B2 | 6/2011 | Fournie | |
| 8,142,418 B2 | 3/2012 | McMichael et al. | |
| 8,316,890 B2 | 11/2012 | Gaus | |
| 8,397,956 B2 | 3/2013 | Olechowski | |
| 2007/0289651 A1 | 12/2007 | Brown et al. | |
| 2008/0027415 A1 * | 1/2008 | Isaacson | A61M 25/0097 604/539 |
| 2010/0286596 A1 * | 11/2010 | Hofmann | A61M 1/008 604/35 |
| 2013/0030387 A1 | 1/2013 | Williams et al. | |

OTHER PUBLICATIONS

Notice of Reasons for Rejection dated Jan. 30, 2018 for corresponding Japanese Application No. 2016-537013 (re-submitting from IDS filed on Mar. 16, 2018).

* cited by examiner

AUTO-SHUTOFF COUPLING

CROSS-REFERENCE TO RELATED APPLICATION

This application claims the benefit of U.S. Provisional Patent Application Ser. No. 61/914,039 filed Dec. 10, 2013, which is incorporated in its entirety herein by reference.

FIELD

The present disclosure relates to a breakaway coupling for use with medical fluids. In particular, the disclosure concerns a breakaway coupling that employs valves to seal each exposed end of the coupling when the coupling is disconnected.

BACKGROUND

In various medical procedures or treatments, tubes are used to provide patients with medicine, nutrition, or other fluids as part of their treatment. Such tubes are used to connect the patient to a fluid supply. For example, tubes are employed in feeding systems which provide nutritional fluids to patients who either require additional supplements to meet dietary needs or who are unable to eat orally. Feedset couplings are used in medical feeding systems for connecting the tubes between a feeding supply source and a patient. Typically the couplings only include a male adapter that mates with a female adapter. When a coupling becomes disconnected (such as when incidental tension is applied to some part of the feeding system), the contents of the supply source can continue flowing uninterrupted out of the tube via the disconnected coupling. Additionally, contents from the patient's gastrointestinal tract may also backflow uninterrupted out of the tube from the patient. A number of problems result from such uninterrupted and unconnected flow including loss of feeding, loss of medication, loss of time in supplying a patient with the necessary nutrition, compromised patient health, clean up, poor sleeping due to wetness and hunger, and potentially patient aspiration on the spilled tube feeding.

Some feeding supply systems include alarms that signal when the supply fluid is "free flowing." However, these alarm systems only work if a supply pump becomes disconnected, not if a feedset coupling becomes disconnected. Accordingly, some manufacturers have tried to prevent the feedset coupling from becoming disconnected. However, these devices can cause the feeding tube to be dislodged from the patient entirely, leading to similar and additional problems.

BRIEF SUMMARY

A simplified summary is provided herein to facilitate a basic or general understanding of various aspects of non-limiting embodiments that follow in the more detailed description and the accompanying drawings. This summary is not intended, however, as an extensive or exhaustive overview. Instead, the sole purpose of the summary is to present some concepts related to some non-limiting embodiments in a simplified form as a prelude to the more detailed description of the various embodiments that follow.

According to one non-limiting example a tube coupling comprises a female adapter integrally attached to a first end of a source tube and the source tube connected to a supply source at a second end of the source tube, the female adapter comprising a one-way valve situated to prevent a flow from a source through the first end of the source tube when the female adapter is uncoupled; and a male adapter attached to a first end of a destination tube, the destination tube connected to a destination at a second end of the destination tube, the male adapter comprising a hollow post that extends away from the destination tube and a one-way valve situated behind the post to prevent backflow of fluid through the first end of the destination tube from the destination when the male adapter is uncoupled, wherein when the male and female adapters are coupled to each other, the hollow post of the male adapter penetrates the one-way valve of the female adapter causing the one-way valve of the female adapter to open, and a flow pressure from the source opens the one-way valve of the male adapter to facilitate an uninterrupted flow from the source through the source tube and the destination tube to the destination.

According to other examples of the above example, the inner and outer diameters of the female adapter and male adapter are equal to or less than that of the inner and outer diameters of the source and destination tubes, respectively; the one-way valve of the female adapter requires at least about 20 psi of back pressure to open; the one-way valve of the male adapter requires at least about 30 psi of back pressure to open; the one-way valves of the female adapter and the male adapter are non-mechanical; the one-way valves of the female adapter and the male adapter are duckbill valves, slit valves, or a combination thereof; the source comprises a medical fluid and the destination is a patient to receive the medical fluid; the female adapter and male adapter further comprise a locking mechanism requiring a pre-determined amount of force to couple and uncouple the female and male adapters; the male adapter further comprises a locking ring and the female adapter further comprises a retention ring such that, when coupled, the locking ring mates with the retention ring; pinching the female adapter releases the locking ring from the retention ring; and the male adapter and destination tube, and female adapter and source tube, are free to rotate with respect to each other.

These and other embodiments are described in more detail below.

DETAILED DESCRIPTION OF THE DRAWINGS

This disclosure relates to a breakaway coupling for lines or tubing that is commonly used to supply medical fluids to a patient. In particular, the breakaway coupling connects two ends of tubing and allows a controlled flow of fluid in one direction. Each end of the coupling is integrated into each end of the tubing to facilitate connecting the ends together. When the two ends are mated to engage the coupling, fluid flows through the coupling in a unidirectional manner. A valve is located at each end of the coupling which seal the respective end of the coupling when the coupling becomes disconnected. Thus, when the coupling is disengaged, the valve on each end of the tubing stops the flow of fluid.

Figure 1:
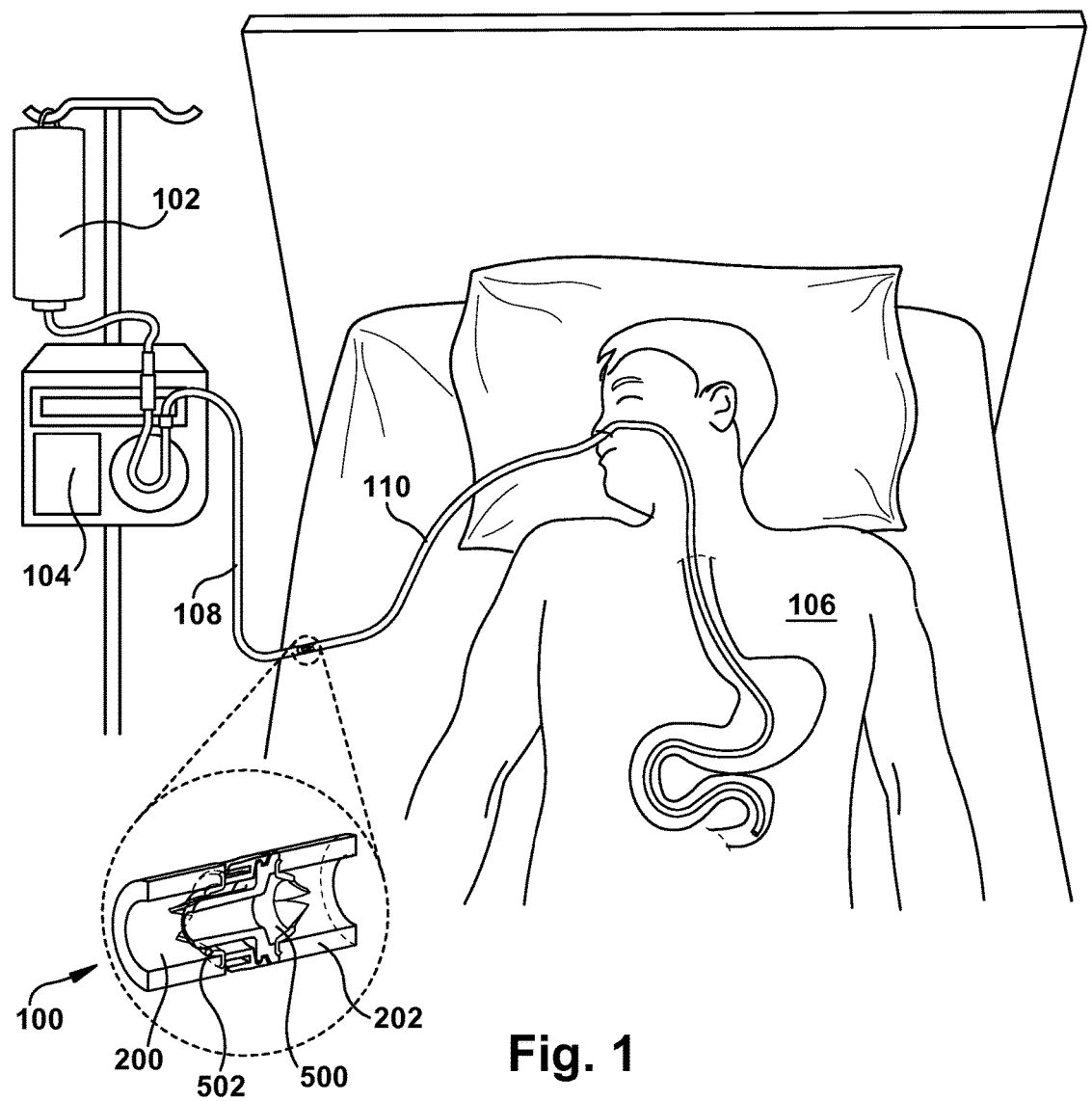
FIG. 1 is a coupling as used in a feeding system.

Turning now to the figures, FIG. 1 illustrates a coupling 100 of the present disclosure used in a feeding system. While the remainder of the disclosure depicts the coupling 100 in the context of a feeding system, it should be understood that the coupling 100 can be incorporated into other types of systems in which disconnection of a line or tube results in an undesirable flow of fluids. For example, in the medical field, the coupling 100 also has utility in any system that supplies a fluid to a patient such as by intravenous delivery.

As shown, a feeding source 102 and associated feeding pump 104 are connected to a patient 106 via a source tube 108 and a destination tube 110 (collectively, tubes 108 and 110 may be referred to as a feeding tube in this example). The coupling 100 is located between the patient 106 and the feeding source 102 and is used to connect the source tube 108 and destination tube 110 together.

The coupling 100 comprises a female adapter 200 and a male adapter 202. The male adapter 202 includes a valve 500, and the female adapter 200 also includes a valve 502. The female adapter is integrally attached to a first end of the source tube 108. Similarly, the male adapter 202 is integrally attached to a first end of the destination tube 110. A second end of the source tube 108 is connected to the source 102 and a second end of the destination tube 110 is connected to a destination 106 (e.g., patient). As depicted in the figure, a pump 104 may be present. When a pump is present and connected in a similar arrangement as illustrated, the second end of the source tube 108 may be connected to the pump 104. It should be appreciated that the configuration of the second end of the source tube 108 does not affect the operation of the coupling 100.

When the female 200 and male 202 adapters are coupled, contents from the feeding source 102 are permitted to flow from the source 102 and pump 104 to the patient 106 in a controlled, unidirectional manner. That is, the fluid is able to flow unencumbered through the valves 500, 502 of the coupling 100 when the female and male adapters are connected to each other. When the female and male adapters are disconnected from one another, the valve 500, such as a one-way valve, located in the male adapter 202 of the coupling 100 prevents the patient's gastric fluid from backflowing (out from the patient) out from the unconnected end of the destination tube 110. Similarly, the valve 502 in the female adapter 200 may also be a one-way valve that becomes engaged or activated when disconnected from the male adapter 202. When the valve 502 is engaged or activated, the flow of fluid from the feeding source is not permitted through the valve 502. Consequently, an accidental disconnection at the coupling 100 will not result in a large mess nor will the patient's health or well-being be compromised.

Figure 2:
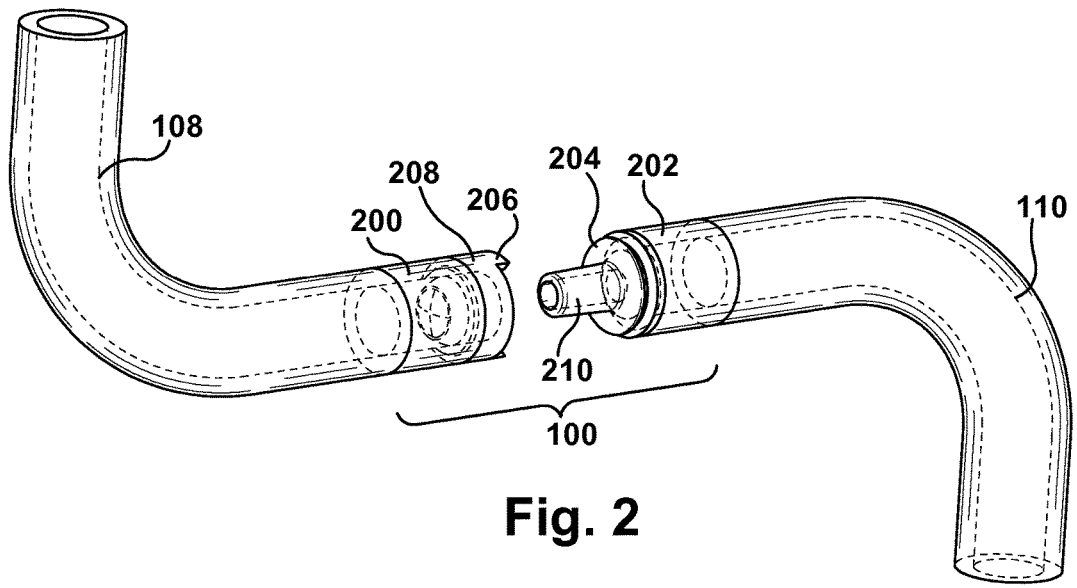
FIG. 2 is a perspective view of a coupling in an uncoupled state.
Figure 3:
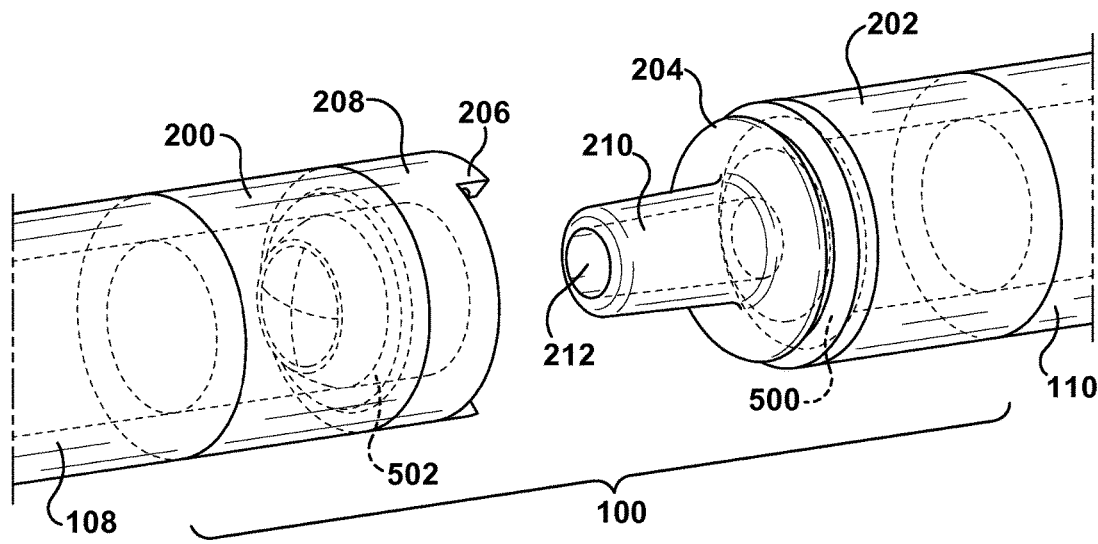
FIG. 3 is an enlarged perspective view of a coupling in an uncoupled state.

The coupling 100 as it is used with respect to a feeding tube or IV line provides greater mobility and ease of movement for the patient while sitting or lying down during treatment or feeding. FIGS. 2 and 3 illustrate perspective views of the coupling 100 in an uncoupled or disconnected state. A source tube 108 is connected to a source or an associated pump (not shown) on one end. At the opposite end, the source tube 108 comprises a female adapter 200 integrated as part of the tube 108. The female adapter 200 end of the tube 208 is one part or half of the coupling 100. Similarly, a destination tube 110 is connected on one end to a destination or a patient (not shown), and to a male adapter 202 of the coupling 100 on the other end. The inner and outer diameters of the female and male adapters and the respective source and delivery tubes, are identical. However, in some embodiments, the outer diameter of the adapter may be equal to or less than the inner diameter of the respective tube; or, the inner diameter of the adapters may be equal to or larger than the outer diameter of the respective tube, as long as contents from the source are not trapped at any point in the tubing as a result.

The male adapter 202 comprises a locking ring 204 that, when fitted in a retention ring 206 of the female adapter 200, engages the male and female adapters 202, 200 together to form the coupling 100. The locking and retention rings 204, 206 are located circumferentially around their respective adapters 202, 200 near the end distal to the respective tubes 110, 108. Accordingly, coupling of the adapters 200, 202 results in coupling of the source and delivery tubes 108, 110. The locking ring and retention rings 204, 206 may include one or more grooves and ridges that fit together in a complimentary manner.

In some embodiments, locking may occur by simply snapping the adapters 200, 202 together by a pre-determined amount of force. Similarly, the coupling 100 can be disconnected by pulling the male and female adapters 202, 200 apart with the same or similar force. In other embodiments, coupling may occur by a pinch and release mechanism. In such embodiments, the female adapter may additionally comprise locking fingers 208. The locking fingers 208 may be located at discrete locations around the female adapter 200 or a single locking finger may be located circumferentially around the entirety of the female adapter 200. An opening behind the locking fingers allows them to be depressed radially inward. When depressed radially inward, the retention ring 206 opens radially outward, thereby allowing the locking ring 204 to be more easily inserted or removed from the retention ring 206. Additionally, the use of locking and retention rings 204, 206 allows the source and destination tubes 108, 110 to rotate with respect to each other as a patient, feeding source, or both move without resulting in any disconnection of the coupling 100 or affecting a flow through the coupling in any way. Both the male and female adapters 202, 200 comprise valves 500, 502, which will be discussed in more detail below. The male adapter 202 further comprises a hollow post 210 that extends away from the destination tube 110. An opening 212 at the tip of the hollow post 210 permits the flow of contents from the source.

Figure 4:
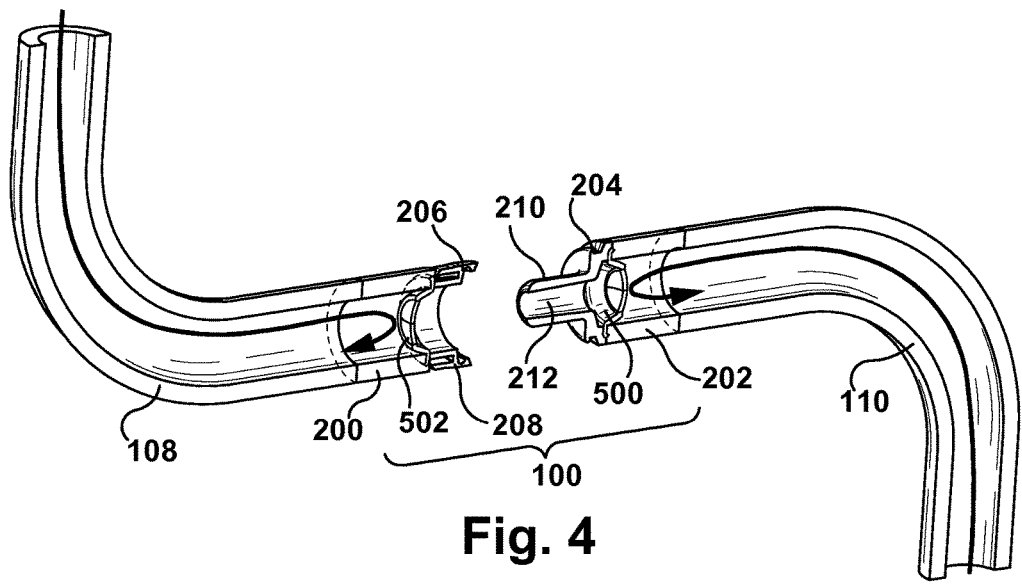
FIG. 4 is a cross-sectional view of a coupling in an uncoupled state.
Figure 5:
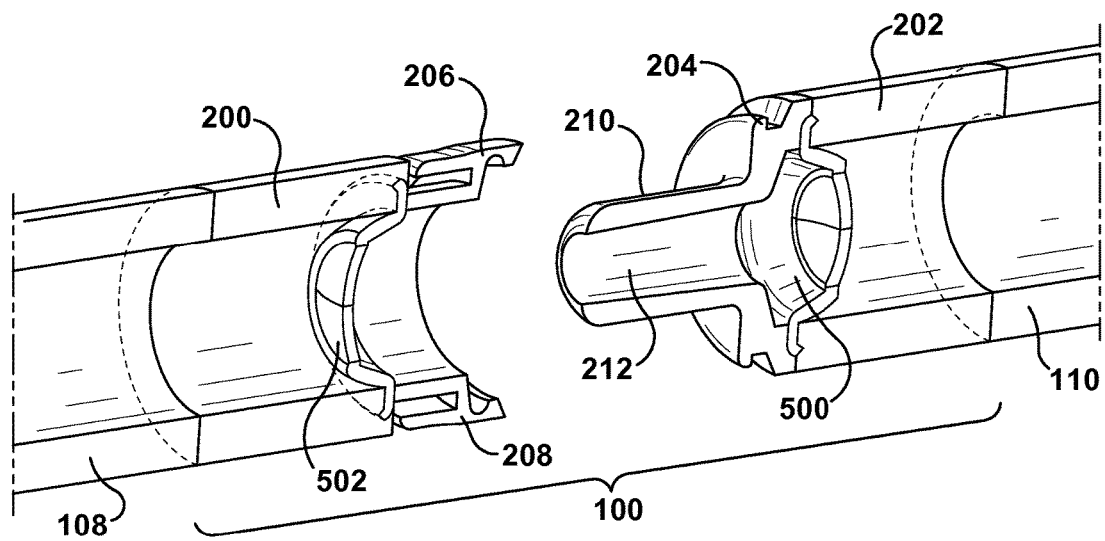
FIG. 5 is an enlarged cross-sectional view of a coupling in an uncoupled state.

FIGS. 4 and 5 illustrate a cross-section of an uncoupled coupling 100 to more clearly show the valves 500, 502 with respect to each adapter. In the illustrated example, the valve 502 of the female adapter 200 is located within the female adapter 200 such that a concave side of the valve 502 is open to the ambient air when uncoupled. The valve 500 of the male adapter 202 rests behind the hollow post 210 such that a concave side of the valve 500 is also open to the ambient air through the post opening 212. The valves 500, 502 are pressure valves, such as one-way valves. The valves may also be constructed such that they contain perpendicular slits that flair open and then collapse when closed, or they may be duck-billed valves. The valve 502 in the female adapter 200 can withstand at least 30 psi of back pressure. Therefore, when uncoupled, the valve can withstand up to a 30 psi flow from a source or associated pump. The valve 500 in the male adapter 202 can withstand at least 20 psi of back pressure, and can open with a range of 0-¼ psi cracking pressure. That is, the valve 500 in the male adapter 202 can withstand gastrointestinal backflow from a patient up to 30 psi when in an uncoupled state, and will be opened with at most a ¼ psi flow from a source or associated pump when in a coupled state.

In sum, based on the above arrangement, when uncoupled, the flow of contents from the source and destination is trapped within the respective tubes 108, 110. Of course, it should be noted that the above valve backflow and cracking pressures are not intended to be limiting. Rather, either valve 500, 502 may have a greater or smaller backflow or cracking pressure depending on the particular application. Additionally, it is noted that the ratio of pressures between the two valves 500, 502 may be varied with other embodiments. The valves 500, 502 may be elastomeric, plastic, silicone, or other fluid flow control material. One type of valve that may be utilized with the example coupling is manufactured by LMS of Midland, Mich., a division of Aptar Group, Inc., which owns a number of patents relating to valve design. Other valves by different manufacturers may alternatively be used.

Figure 6:
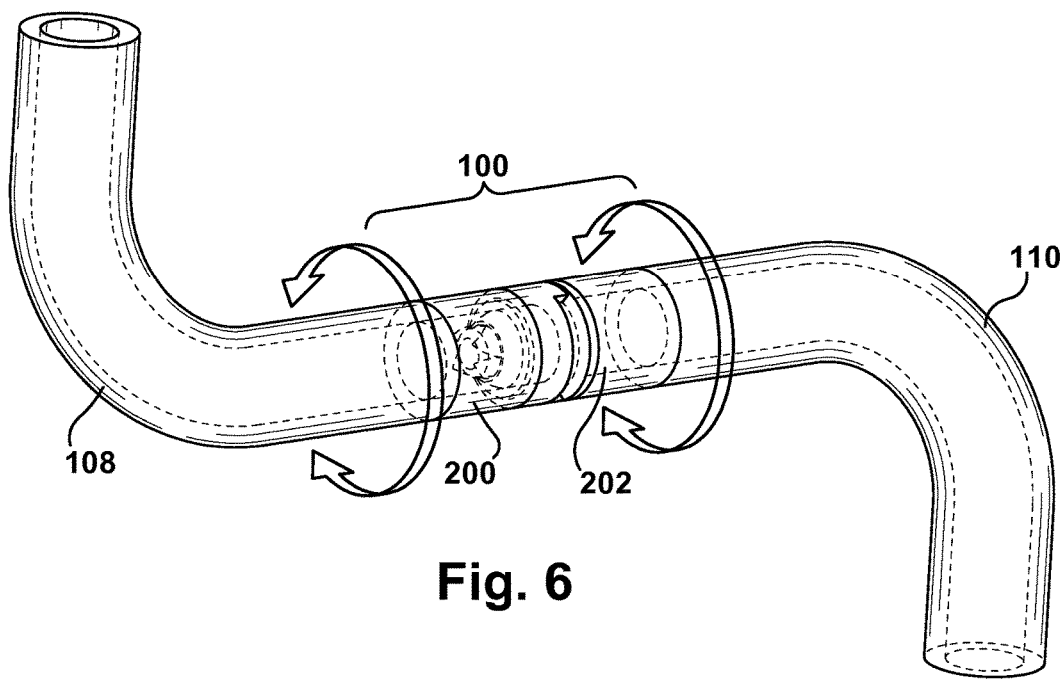
FIG. 6 is a perspective view of a coupling in a coupled state.
Figure 7:
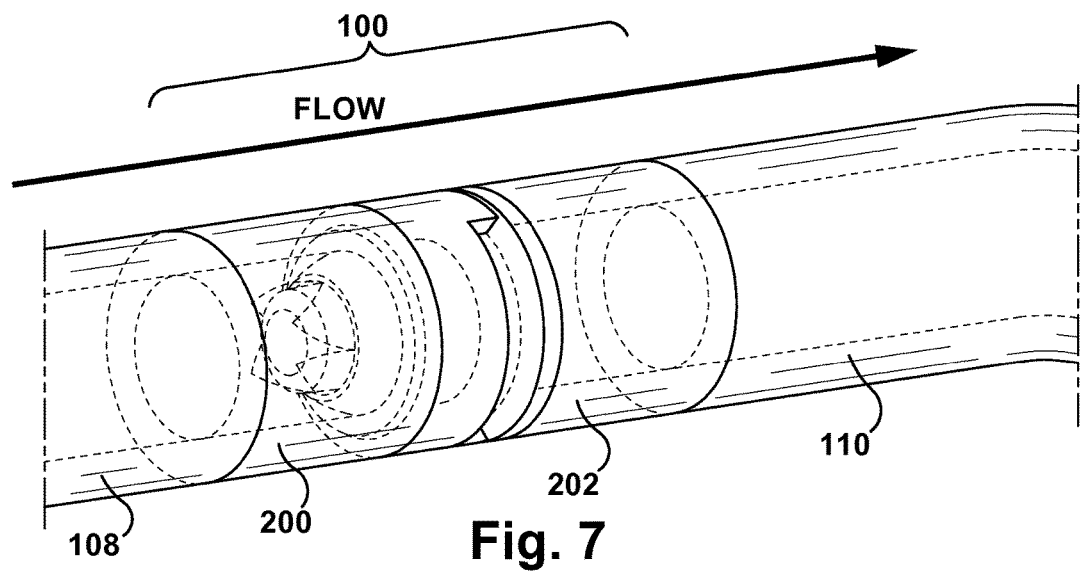
FIG. 7 is an enlarged perspective view of a coupling in a coupled state.

Referring now to FIGS. 6 and 7, the coupling 100 is illustrated in a connected state. As discussed above, the locking ring 204 of the male adapter 202 fits within the retention ring 206 of the female adapter 200 in the connected state. This allows the source and destination tubes 108, 110 to rotate with respect to each other as a patient, feeding source, or both move, without resulting in an undesirable disconnection of the coupling 100 or adversely affecting a flow of content from the source through the coupling 100 due to such movement.

Figure 8:
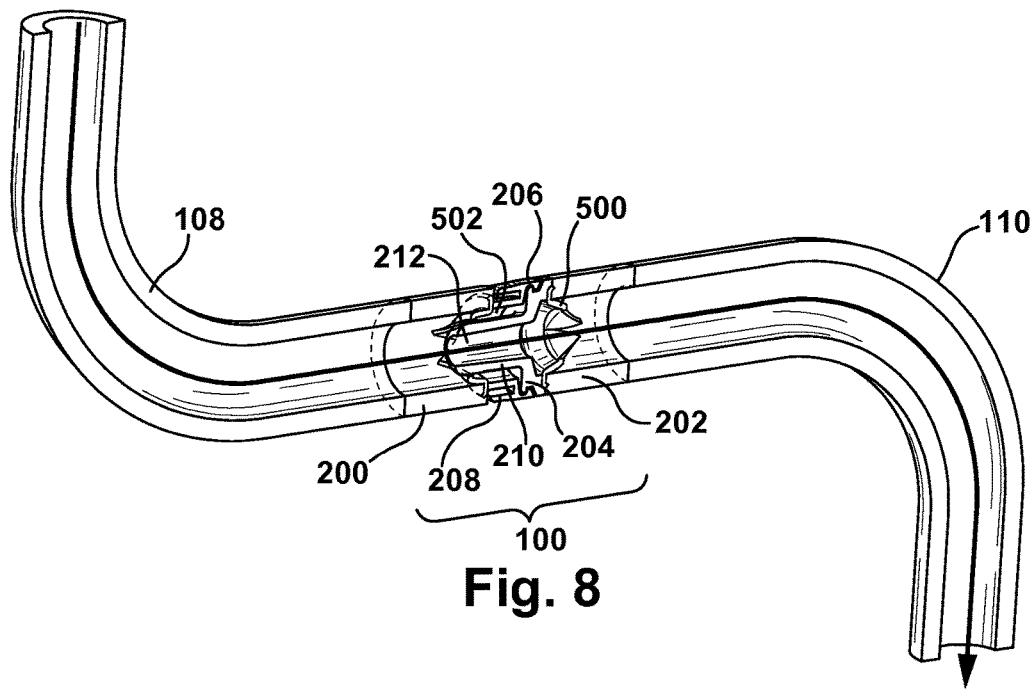
FIG. 8 is a cross-sectional view of a coupling in a coupled state.
Figure 9:
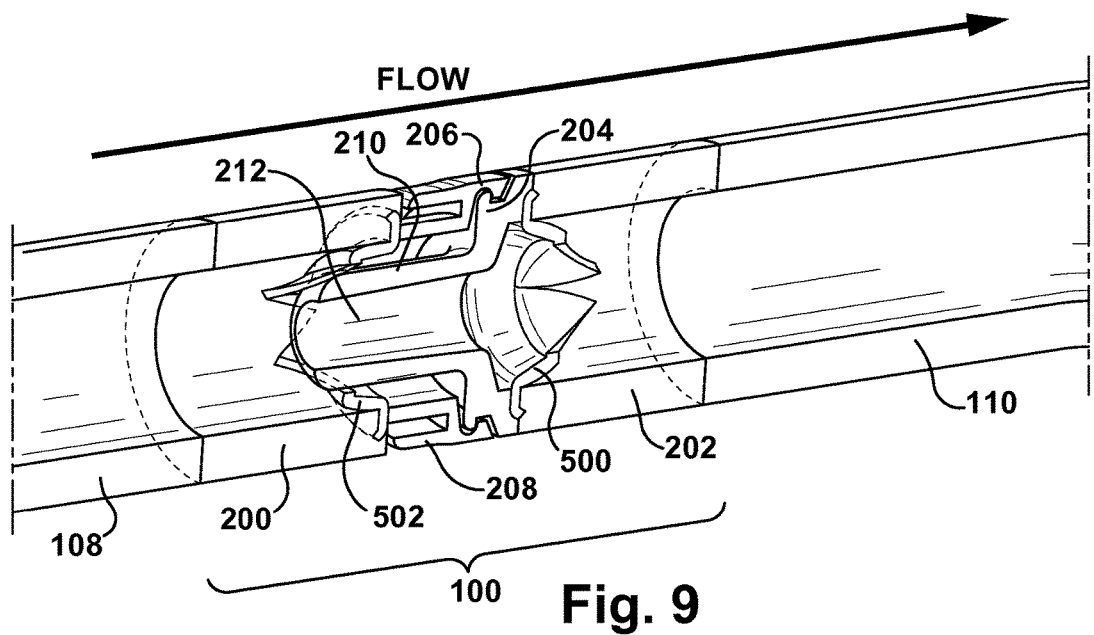
FIG. 9 is an enlarged cross-sectional view of a coupling in a coupled state.

As shown in FIGS. 8 and 9, when the male and female adapters 202, 200 are coupled, the hollow post 210 of the male adapter 202 penetrates the valve 502 of the female adapter 200, thereby opening the valve 502 of the female adapter 200. As indicated by the arrow, a flow of contents from the source may continue through the source tube 108, into the post 210, and with enough pressure, opens the valve 500 of the male adapter 202 where it continues through the destination tube 110 to the patient. When the male adapter 202 is removed, the valve 502 of the female adapter 200 closes because the post 210 is no longer penetrating the valve 502. Accordingly, removal of the post 210 prevents further flow of contents out of the source tube 108 or into the male adapter 202 and destination tube 110. Without continued flow, the valve 500 of the male adapter 202 closes, thereby preventing backflow from the destination.

Certain terminology used herein is for convenience only and is not to be taken as a limitation on the present invention. Relative language used herein is best understood with reference to the drawings, in which like numerals are used to identify like or similar items. Further, in the drawings, certain features may be shown in somewhat schematic form.

While various features of the claimed invention are presented above, it should be understood that the features may be used singly or in any combination thereof. Therefore, the claimed invention is not to be limited to only the specific embodiments depicted herein.

Further, it should be understood that variations and modifications may occur to those skilled in the art to which the claimed invention pertains. The embodiments described herein are exemplary of the claimed invention. The disclosure may enable those skilled in the art to make and use embodiments having alternative elements that likewise correspond to the elements of the invention recited in the claims. The intended scope of the invention may thus include other embodiments that do not differ or that insubstantially differ from the literal language of the claims. The scope of the present invention is accordingly defined as set forth in the appended claims.

What is claimed is:

1. A tube coupling comprising:
    a female adapter attached to a first end of a source tube and the source tube connected to a supply source at a second end of the source tube, the female adapter comprising a one-way valve situated to prevent a flow from a source through the first end of the source tube when the female adapter is uncoupled; and
    a male adapter attached to a first end of a destination tube, the destination tube connected to a destination at a second end of the destination tube, the male adapter comprising a hollow post that extends away from the destination tube and a one-way valve situated behind the post to prevent backflow of fluid through the first end of the destination tube from the destination when the male adapter is uncoupled,
    wherein when the male and female adapters are coupled to each other, an end of the hollow post of the male adapter penetrates the one-way valve of the female adapter causing the one-way valve of the female adapter to open,
    a flow from the source passes through the hollow post and has a pressure that forces open the one-way valve of the male adapter, thereby facilitating an uninterrupted flow from the source through the source tube and the destination tube to the destination,
    the end of the hollow post that penetrates the one-way valve of the female adapter is distal to the one-way valve situated behind the post, and comprises an opening that is uncovered when the male adapter and the female adapter are both coupled and uncoupled, and
    an inner diameter of the female adapter is constant through a portion comprising the one-way valve therein, and an inner diameter of the male adapter is constant through a portion comprising the one-way valve therein.

2. The coupling of claim 1, wherein the inner and outer diameters of the female adapter and male adapter are equal to that of the inner and outer diameters of the source and destination tubes, respectively.

3. The coupling of claim 1, wherein the one-way valve of the female adapter requires at least about 20 psi of back pressure to open.

4. The coupling of claim 1, wherein the one-way valve of the male adapter requires at least about 30 psi of back pressure to open.

5. The coupling of claim 1, wherein the one-way valves of the female adapter and the male adapter are duckbill valves, slit valves, or a combination thereof.

6. The coupling of claim 1, wherein the source comprises a medical fluid and the destination is a patient to receive the medical fluid.

7. The coupling of claim 1, wherein the female adapter and male adapter further comprise a locking mechanism requiring a pre-determined amount of force to couple and uncouple the female and male adapters.

8. A tube coupling comprising:
    a female adapter attached to a first end of a source tube and the source tube connected to a supply source at a second end of the source tube, the female adapter having a lumen comprising a one-way valve situated in the lumen to prevent a flow from a source through the first end of the source tube when the female adapter is uncoupled; and a male adapter attached to a first end of a destination tube, the destination tube connected to a destination at a second end of the destination tube, the male adapter comprising a hollow post that extends away from the destination tube and a one-way valve situated behind the post to prevent backflow of fluid through the first end of the destination tube from the destination when the male adapter is uncoupled, wherein when the male and female adapters are coupled to each other, the hollow post of the male adapter penetrates the one-way valve of the female adapter causing the one-way valve of the female adapter to open, and a flow from the source passes through the hollow post and has a pressure that forces open the one-way valve of the male adapter, thereby facilitating an uninterrupted flow from the source through the source tube and the destination tube to the destination, wherein the male adapter further comprises a locking ring and the female adapter further comprises a retention ring, and wherein the retention ring is a recess on an inner surface of the lumen of the female adapter such that, when coupled, the locking ring mates within the retention ring.

9. The coupling of claim 8, wherein the female adapter comprising a locking finger that, when depressed radially inward, releases the locking ring from the retention ring by opening the retention ring radially outward.

10. The coupling of claim 8, wherein the locking ring is unencumbered within the retention ring such that the male adapter and the female adapter are free to rotate with respect to each other.

* * * * *